(12) United States Patent
Veenstra et al.

(10) Patent No.: US 7,229,780 B2
(45) Date of Patent: Jun. 12, 2007

(54) MONOCLONAL ANTIBODY AGAINST OVARIAN CARCINOMA

(75) Inventors: Hannelore F. U. Veenstra, Panorama (ZA); Catharina E. Fick, Camps Bay (ZA)

(73) Assignees: The Medical Research Council, Parow Valley (ZA); Stellenbosch University, Matieland (ZA)

( * ) Notice: Subject to any disclaimer, the term of this patent is extended or adjusted under 35 U.S.C. 154(b) by 51 days.

(21) Appl. No.: 10/488,774

(22) PCT Filed: Sep. 4, 2001

(86) PCT No.: PCT/ZA01/00132

§ 371 (c)(1),
(2), (4) Date: Mar. 5, 2004

(87) PCT Pub. No.: WO02/20620

PCT Pub. Date: Mar. 14, 2002

(65) Prior Publication Data

US 2004/0259174 A1     Dec. 23, 2004

(30) Foreign Application Priority Data

Sep. 5, 2000    (ZA)   ................................. 2000/2782

(51) Int. Cl.
    *G01N 33/577*     (2006.01)
(52) U.S. Cl. ...................... 435/7.23; 436/518; 436/501; 530/388.1; 435/326
(58) Field of Classification Search ............. 530/387.1; 435/354, 4, 7.1, 7.23, 325
See application file for complete search history.

(56) References Cited

FOREIGN PATENT DOCUMENTS

WO     WO 88/03954     6/1988
WO     WO 89/01629     2/1989

OTHER PUBLICATIONS

Sell, Stem cell origin of cancer and differntiation therapy. Critical Reviews in Oncology/Hematology, vol. 51, pp. 1-28, Jul. 2004.*
Cho & Leahy, Structure of the extracellular region of HER3 reveals an interdomain tether, Aug. 2002, Science vol. 297, ages 1330-1333, with commentary by Patrice Pages.*
Piek et al., Intraperitoneal serous adenocarcinoma: a critical appraisal of three hypotheses on its cause. Am J Obstetrics Gynecol vol. 191, pp. 718-732, Sep. 2004.*
Roitt, et al., Immunology, 6th Edition, Jun. 2001, pp. 65-85.*
McCluggage, Recent advances in immunohistochemistry in the diagnosis of ovarianneoplasm F. Clin Pathol, 2000, vol. 53, pp. 327-334.*
Kurosaka et al., Production of monoclonal antibodies recognizing cancer-associated antigens expressed on mucin-type sugar chains. Biochem Biophys Res comm, vol. 203, No. 3, pp. 1828-1834. Sep. 1994.*

McCluggage et al, monoclonal antibody SM047 as an immunohistochemical marker of ovarian adenocarcinoma. 2001. Histopathology vol. 38, 542-549.*
Bell, Origins and molecular pathology of ovarian cancer. 2005. Modern Pathology vol. 18, pp. S19-S32.*
Kurosaka et al., "Production of Monoclonal Antibodies, Recognizing Cancer-Associated Antigens Expressed on Mucin-Type Sugar Chains", Biochemical and Biophysical Research Communications, Vo. 203, No. 3, pp. 1828-1834, Sep. 30, 1994.
McCluggage et al., "Monoclonal antibody SM047 as an immunohistochemical marker of ovarian adencarcinoma", Histopathology 2001, 38, 542-549.
McCluggage, "Recent advances in immunohistochemistry in the diagnosis of ovarian neoplasms", F. Clin. Pathol. 2000; 53:327-334.
Cheung et al., "Is Immunostaining With HAM56 Antibody Useful in Identifying Ovarian Origin of Metastatic Adencarcinomas?", Huamn Pathology, vol. 28, No. 1, pp. 91-94, Jan. 1997.
Loy et al., "Distribution of CA 125 in Adencarcinomas", A.J.C.P., Aug. 1992, pp. 175-179.
Wauters et al., "Keratins 7 and 20 as Diagnostic Markers of Carcinomas Metastatic to the Ovary", Human Pathology, vol. 26, No. 8, pp. 852-855, Aug. 1995.
Berezowski et al., "Cytokeratins 7 and 20 and Carcinoembryonic Antigen in Ovarian and Colonic Carcinoma", Modern Pathology, pp. 426-429.
Golombick et al., "Establishment and Characterization of Two New Human Ovarian Cancer Cell Lines . . . ", Cell. Dev. Biol. 26:447-454, May 1990.
Warren et al., "Membranes of Animal Cells", J. Cell. Physiol., 68:269-288.
Veenstra et al., "Multi-well cell monolayers for immunocytochemistry", Journal of Immunological Methods, 146 (1992), pp. 257-258.
Jones, "Analysis of Radiolabeled Lymphocyte Proteins by One- and Two-Dimensional Polyacrylamide Gel Electrophoresis", pp. 398-440.
Bayer et al., "Analysis of Proteins and Glycoproteins on Blots", Methods in Enzymology, Vol. 184, pp. 415-427.
Biosynthetic Labelling of Proteins, Current Protocols in Immunology, Unit 8.12.1-8.12.9.
Young et al., "Metastases from Carcinomas of the Pancreas Simulating Primary Mucinous Tumors of the Ovary", The American Journal of Surgical Pathology, 13(9); pp. 748-756, 1989.
Jacobs et al., "Clinical Review: The CA 125 tumour-associated antigen: a review of the literature", Human Reproduction, vol. 4, No. 1, pp. 1-12, 1989.
Nouwen et al., "Immunohistochemical Localization of Placental Alkaline Phorphatase, Carcinoembryonic Antigen, . . . ", Cancer Research, vol. 46, Feb. 1986, pp. 886-876.

\* cited by examiner

*Primary Examiner*—Misook Yu
(74) *Attorney, Agent, or Firm*—B. Aaron Schulman; Stites & Harbison PLLC

(57) ABSTRACT

The present invention provides a monoclonal antibody designated SM047 against cancer, specifically ovarian carcinoma. SM047 is strongly expressed in most ovarian serous adenocarcinomas and in other female genital tract adenocarcinomas. The monoclonal antibody according to the invention is useful to detect a cancer, specifically ovarian carcinoma and/or or determine the origin of cancer. The present invention also provides a hybridoma cell producing the monoclonal antibody and an antigen which binds to the monoclonal antibody according to the present invention.

14 Claims, 5 Drawing Sheets

MONOCLONAL ANTIBODY AGAINST OVARIAN CARCINOMA

FIELD OF THE INVENTION

The present invention is directed to a monoclonal antibody against cancer, specifically ovarian carcinoma. The present invention is also directed to a hybridoma cell producing the monoclonal antibody and an antigen which binds to the monoclonal antibody according to the present invention. The present invention relates to a method of detecting a cancer, specifically ovarian carcinoma or determining the origin of cancer and a diagnostic aids.

BACKGROUND TO THE INVENTION

Ovarian carcinoma is disease that eludes early diagnosis and has a high mortality rate. In a diagnosis of ovarian carcinoma, one of the most common problem is to distinguish between a primary ovarian and colorectal adenocarcinoma. Colorectal adenocarcinomas metastatic to the ovary may closely resemble primary ovarian endometrioid or mucinous adenocarcinomas [1] and the morphological distinction is difficult.

Monoclonal antibodies raised against tumour-associated antigens have been widely used in pathological practice, especially in the determination of the likely primary site of an adenocarcinoma when this is not known clinically. In the case of ovarian cancer these antibodies have not proven sufficiently specific and their value is limited in a diagnostic sense. Antibodies such as CA125 and human alveolar macrophage (HAM) 56 have been proposed as useful immunohistochemical markers of ovarian adenocarcinoma but immunoreactivity is often present in adenocarcinomas of other sites, limiting their diagnostic value. [2,3] Anticytokeratin (CK) antibodies are of value in certain diagnostic situations, especially in the distinction between a primary ovarian adenocarcinoma (usually CK7+, CK20−) and a colonic adenocarcinoma (usually CK7−, CK20+). [4,5] However, these antibodies are of no value in the distinction between an ovarian primary and an adenocarcinoma arising in the stomach, breast, pancreas or biliary tree, since these tumours share a common anti-CK immunoprofile.

In addition, the serological test using CA125 has been used for monitoring disease progression or recurrence after treatment but it is not sensitive enough for early detection of such tumours and gives false positive results in other clinical conditions. The CA125 MAb cannot be used for immunocytochemical detection in routine pathological specimen, as it does not react with the denatured antigen in these tissues.

Accordingly, a need exists to provide an improved diagnostic tool and method for detecting an ovarian carcinoma cell.

BRIEF DESCRIPTION OF THE INVENTION

According to one aspect of the present invention a monoclonal antibody, designated SM047, which is specifically reactive against ovarian carcinoma is provided.

More particularly, the present invention provides a monoclonal antibody which binds to an epitope that is displayed by a multivalent antigen associated with the glycocalyx of ovarian carcinoma cells.

According to a further aspect of the present invention a hybridoma cell producing a monoclonal antibody SM047 is provided.

The present invention also provides an antigen which binds to the monoclonal antibody according to the present invention.

According to a still further aspect of the present invention there is provided a method of detecting a carcinoma or determining the origin of carcinoma by using monoclonal antibody SM047. The method according to the present invention includes serological and histochemical detection.

The present invention also provides a diagnostic aid for detecting a carcinoma or determining the origin of carcinoma.

DETAILED DESCRIPTION OF THE INVENTION

Figure 1:
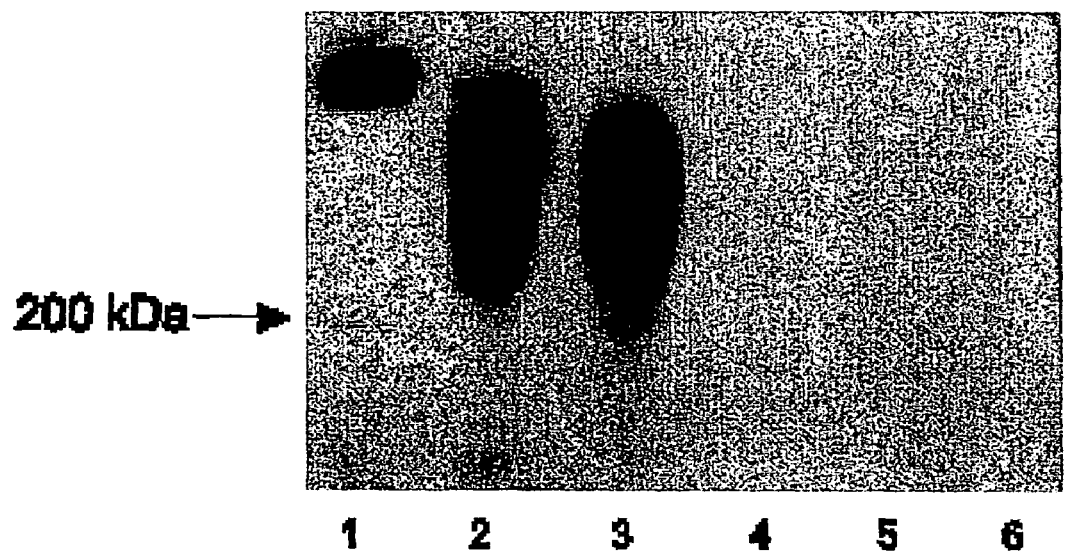
FIG. 1 shows SM047 immunoprecipitates immunoblotted with SM047. *Staphylococcus aureus* was obtained with rabbit anti-mouse immunoglobulin and SM047 Mab as described in Example 1 and added to 100 μl UWOV1 lysate or 50 μl serum from a patient with ovarian malignancy or 50 μl pooled normal serum. After 1 h on ice the particles were washed, boiled with reducing SDS sample buffer and electrophoresed in a 4.5–15% gradient. The proteins in the gel were transferred electrophoretically to PVDF membrane which was blocked and probed with SM047 and peroxidase detection system with chemiluminescent substrate. Lanes 1 and 4 contain SM047 immunoprecipitate from UWOV1 cells, lanes 2 and 5 from a patient's serum and lanes 3 and 6 from a pool of five normal sera. Lanes 1–3 were probed with SM047 and lanes 4–6 with J138 control antibody.

The monoclonal antibody according to the invention, designated SM047 is murine IgM monoclonal antibody produced from hybridoma cells derived from fusion of SP2 myeloma cells with splenocytes of a mouse that had been immunized with a membrane preparation of tumour (ovarian serous cystadenocarcinoma) and boosted with cells from a cell line established from a similar tumour in a different patient.

The hybridoma cell line according to the invention producing the monoclonal antibody SM047 has been deposited with the European Collection of Cell Cultures (ECACC) at Health Protection Agency, Centre for Emergency Preparedness and Response, Porton Down, Salisbury, Wiltshire, SP4 OJG, UK, under the accession no. 01082905 in accordance with the Budapest Treaty.

The monoclonal antibody SM047 binds to an epitope that is displayed by a multivalent antigen associated with the glycocalyx of ovarian adenocarcinoma cells. The present invention also describes SM047 staining in adenocarcinomas of diverse sites in order to determine whether the antibody is specific for ovarian adenocarcinoma and of value in the confirmation of an ovarian origin when the site of primary tumor is unknown. As SM047 staining is specific for an ovarian primary, it is useful in determining the origin of an adenocarcinoma when this is not certain on clinical and pathological grounds.

SM047 is strongly expressed in most ovarian serous adenocarcinomas and in other female genital tract adenocarcinomas, with the exception of ovarian mucinous tumours. SM047 is useful in confirming the ovarian origin of an adenocarcinoma when used as part of a larger panel. This is especially so in the distinction between a non-mucinous ovarian adenocarcinoma, which usually exhibits strong membranous staining, and a colonic adenocarcinoma which is usually negative or exhibits weak cytoplasmic staining.

SM047 is useful for detecting an antigen in the serum of patients with ovarian cancer. SM047 immunoprecipitates the tumour antigen in the sera of patients with ovarian tumours SM047 as well as a "normal" form of the antigen. However, such antigens derived from normal cells are distinguishable from those of tumor cells by its heterogeneous and higher electrophoretic mobility and lack of sialic acid residues. Therefore, the process of detecting an ovarian carcinoma by using SM047 according to invention comprises using a detecting reagent which reacts primarily with the sialic acid-containing tumour-associated SM047 antigen but not or only minimally with the normal form.

The monoclonal antibody SM047 according to the invention is also suitable for immunohistological detection of an ovarian carcinoma. The epitope is not denatured by the formalin fixation and wax embedding procedure to which routine pathology specimens are subjected and this characteristic makes the antibody a useful diagnostic reagent for pathologists in the identification tumours.

The antigen which binds to the monoclonal antibody according to the invention has an electrophorectic mobility of >200 kDa, and electrophoretically homogeneous when associated with tumours, but heterogeneous and of higher mobility in sera of normal individuals. And the antigen has sialic acid residues on the tumour-associated molecules and a fraction of those present in the sera from patients with tumours but not on the molecules present in sera from normal individuals, and has sulphation of the tumour-associated form.

EXAMPLE 1

Development and Characterization of SM047 a. Producing and Purifying SM047

The UWOV1 cell line[6] was kindly supplied by Dr T. Golombick of the University of the Witwatersrand, South Africa.

SM047, an IgM monoclonal antibody (Mab), was the product of hybridoma cells derived by fusion of SP2 myeloma cells with splenic lymphocytes of a mouse that had been immunized with a membrane preparation[7] of an ovarian serous cystadenocarcinoma, boosted once with cells from a cell line derived from that tumour and once with cells from the UWOV1 cell line which was derived from a similar tumour.[6] The hybridomas were produced using essentially standard procedures with the exception that human umbilical cord serum replaced the fetal calf serum in the culture medium. An ELISA assay was used to screen hybridoma-conditioned media for antibodies reactive with UWOV1 cells that had been cultured in 96-well plates and fixed with 0.1% glutaraldehyde, as well as indirect immunofluoresence with dried monolayers of the cells on multiwell Teflon-coated slides.[8]

b. Preparing Cell Lysates

Cells were washed twice with PBS and suspended at $4 \times 10^6$/ml in lysis buffer (PBS containing 0.5% Nonidet P-40, 1 mM phenylmethylsulphonyl fluoride and 2 mM EDTA). Ater 20–30 min on ice the lysates were configured at 12 000 g and the supernatant samples stored at −80° C.

c. Electrophoresis and Immunoblotting

Immunoprecipitates were boiled with reducing SDS sample buffer and electrophoresed in polyacrylamide gels containing 0.1% SDS (SDS-PAGE), using the Laemmli buffer system.[9] The resolved proteins were transferred electrophoretically to PVDF membrane in a semidry apparatus in 0.025 M Tris, 0.192 M glycine in 20% methanol at 1 mA per cm² of gel. The membranes were dried overnight and processed for the identification of Mab-reactive epitopes by blocking and incubating with Mab (hybridoma-conditioned medium 1:10). Bound antibody was detected by exposure to X-ray film after sequential treatment with biotinylated rabbit anti-mouse immunoglobulin (0.55 µg/ml), streptavidin-peroxidase (0.16 µg/ml) and chemiluminescent substrate supplied by Boehringer-Mannheim. All dilutions were made in blocking solution supplied with the substrate and the blots were washed in Tris-buffered saline pH7.6 containing 0.05% Tween 20 between incubations. An IgM anti-mycoplasma Mab (J138), raised in the laboratory, was used as a control antibody. Immunoprecipitates were analysed for sialylated carbohydrate constituents by SDS-PAGE, electroblotting to PVDF membrane labelling with biotin hydrazide after oxidation with sodium metaperiodate at 4° C.[10] according to the instructions of the manufacturers (AEC, Amersham, UK). The labelled carbohydrate was detected with streptavidin-peroxidase and chemiluminescent substrate as for immunoblots.

d. Immunoprecipitation

Formalin-fixed *Staphylococcus aureus* bacteria (SA) at 10% w/v were washed twice in PBS containing 0.5% Nonidet P-40 and 0.02% sodium azide (SA buffer), resuspended at 10% in SA buffer containing 1 mg/ml ovalbumin (SA blocking solution) and incubated on ice for 30 min. One-tenth volume of rabbit anti-mouse immunoglobulin (at 15 mg/ml) was added and the SA left for a further 30 min on ice. The pellets were then washed twice with SA buffer, resuspended in 10× the original volume of SM047 hybridoma conditioned medium and set on ice for a further 30 min. The SA pellet was again washed twice in SA buffer and resuspended at 10% in blocking solution. Cell lysates, sera or UWOV1-conditioned medium were immunoprecipitated with Mab-coated SA for 1 h on ice and washed 3× with SA buffer. Pellets were stored at −20° C. until SDS-PAGE.

EXAMPLE 2

The Preparation of Pathological Specimens

The surgical specimens used in the study for immunohistochemical analysis are shown in Table 1. Specimens had been fixed in 10% unbuffered formol saline or neutral buffered formol saline and routinely processed in paraffin wax. Nine of the ovarian mucinous adenocarcinomas were endocervical in type and the other 14 were enteric in type.

EXAMPLE 3

Immunohistochemical Staining and Analysis

Sections from paraffin wax-embedded blocks were cut onto amino-propyltriethoxysilane-treated slides (Sigma, Poole, UK) and dried overnight at 37° C. Endogenous peroxidase activity was blocked in 3% alcoholic hydrogen peroxide for 10 min. Sections were pretreated in 0.1% trypsin in 0.1% calcium chloride at 37° C. and pH 7.8 or 8 for 10 or 20 min (the immunostaining was performed at several different institutions and was optimised in each of these laboratories. Sections were stained using the Mab SM047 at a dilution of 1:10. Localization was performed using the peroxidase-streptavidin-biotin. Duet system (1:200; Dako, Glostrup, Denmark). Diaminobenzidine (Dako) was used as the chromagen and sections were counterstained using Harris' haematoxylin. Immunohistochemical staining was performed using appropriate positive and negative controls. The positive control consisted of an ovarian serous adenocarcinoma with known diffuse strong membranous immunoreactivity for SM047. For negative controls, the primary antibody was omitted and replaced with mouse isotype immunoglobulin IgM (Dako) at a concentration equal to the primary antibody.

The intensity of staining was classified as negative, weak, moderate or strong. Staining was also classified depending on the percentage of cells exhibiting positivity as 0 (negative), +(0–25% of cells positive), ++(26–50% of cells positive), +++(51–75% of cells positive) or ++++(>75% of cells positive). Positivity was further categorized as predominantly involving the cell membrane or the cell cytoplasm.

Figure 3:
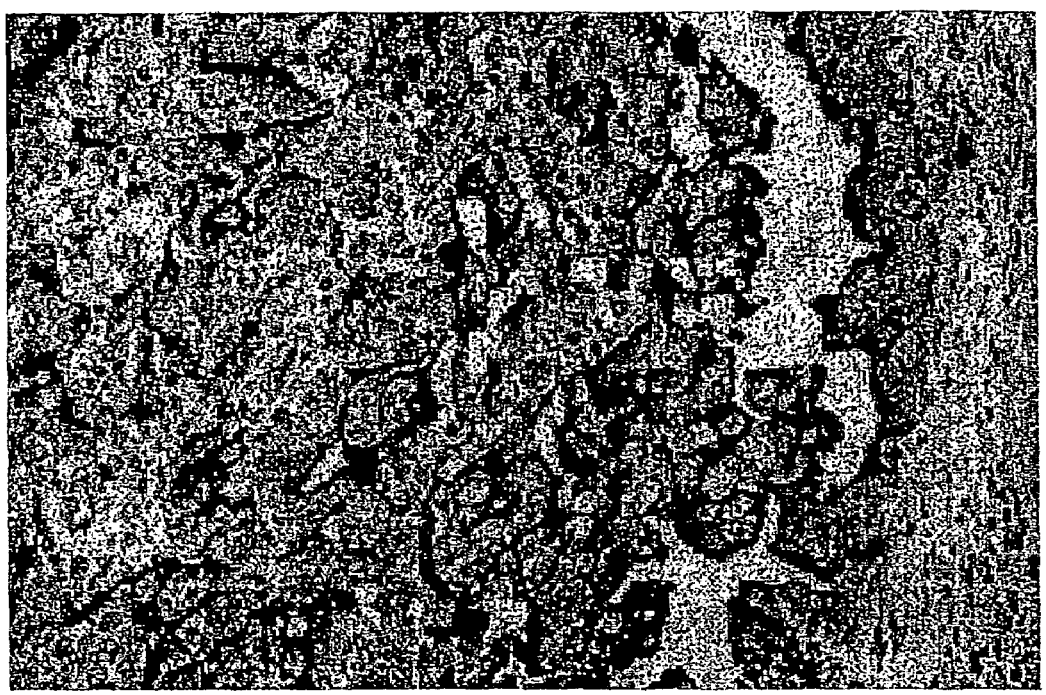
FIG. 3 shows a strong positive membrane staining of ovarian serious adenocarcinoma with SM047.

Immunohistochemical Staining Results:

Table 1 shows the results of the immunohistochemical staining. Twenty-seven of 28 ovarian serous adenocarcinomas exhibited positivity which was usually strong and widespread and which involved the cell membrane (FIG. 3). Positivity was most pronounced in well-differentiated tumours and there was often no staining in poorly differentiated areas. The single ovarian serous adenocarcinoma which was completely negative was extremely poorly differentiated. Moderate or strong positive membranous staining was found in the five ovarian endometrioid and the six clear cell adenocarcinomas. Sixteen of 23 primary ovarian mucinous tumours were completely negative, the others usually exhibiting focal weak positivity which was predominantly cytoplasmic. Three of the four endocervical typers of ovarian mucinous adenocarcinomas were negative, the other case exhibiting positive membranous staining and 51–75% of tumour cells.

Figure 4:
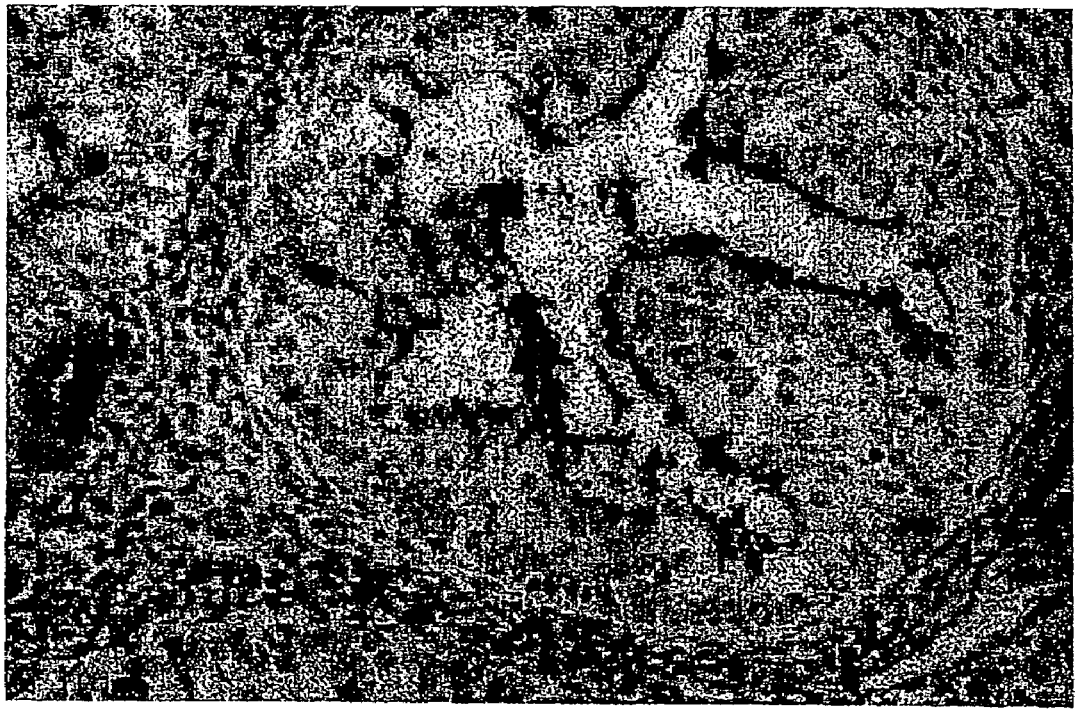
FIG. 4 shows a strong positive membrane staining of endometrioid type endometrial adenocarcinoma with SM047.

There was moderate or strong membranous staining of the 12 endometrial adenocarcinomas (10 endometrioid and two papillary serous) (FIG. 4) and of five of seven endocervical adenocarcinomas. There was positive staining of some pancreatic (four of six), gastric (four of nine) and pulmonary adenocarcinomas (one of four).

Figure 5:
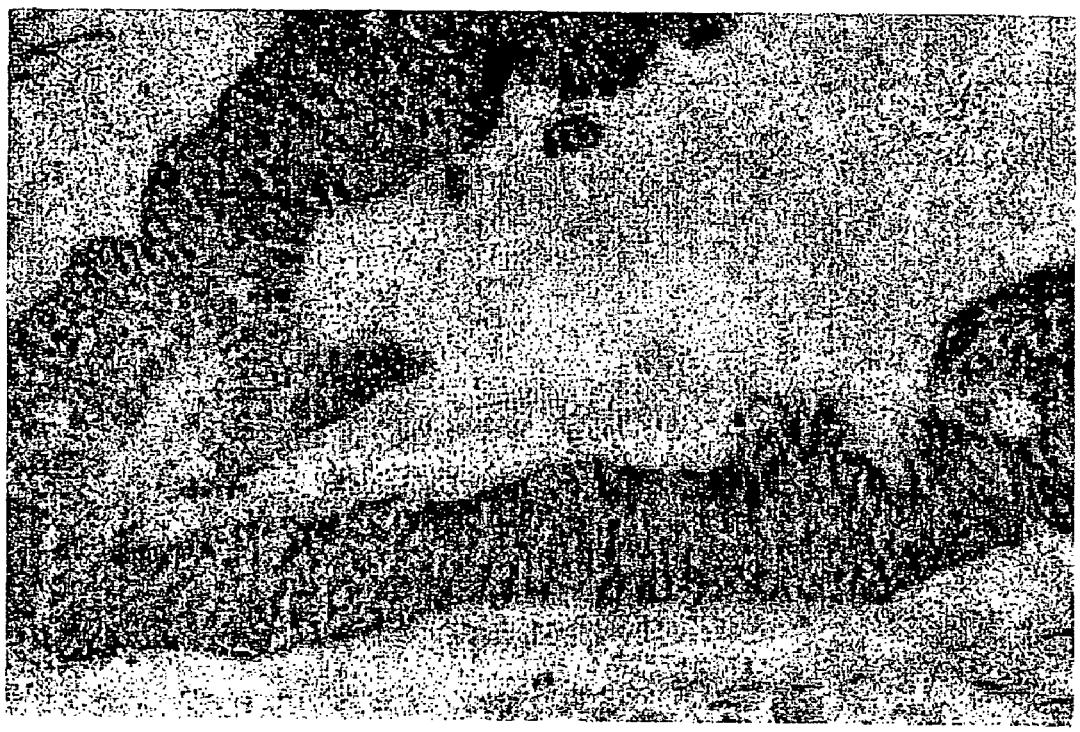
FIG. 5 shows a weak cytoplasmic staining with SM047 in this colonic adenocarcinoma.

Most other adenocarcinomas were completely negative, with the exception of six colonic adenocarcinomas, where staining was usually weak and cytoplasmic (FIG. 5). There was positive staining of four of 10 mesotheliomas in addition to strong membranous staining of normal ovarian surface mesothelium. There was no staining of negative control material.

TABLE 1

Specimens included in study together with immunohistochemical staining results

| Tumour | Staining intensity | | | | Percentage positivity | | | | | Membranous | Cytoplasmic |
|---|---|---|---|---|---|---|---|---|---|---|---|
| | Neg | Weak | Mod | Strong | 0 | + | ++ | +++ | ++++ | | |
| Serous adenocarcinoma ovary ($\eta$ =28) | 1 | 1 | 4 | 22 | 1 | 5 | 5 | 5 | 12 | 27 | 0 |
| Mucinous adenocarcinoma ovary ($\eta$ =23) | 16 | 4 | 3 | 0 | 16 | 6 | 0 | 1 | 0 | 2 | 5 |
| Endometrioid adenocarcinoma ovary ($\eta$ = 5) | 0 | 0 | 1 | 4 | 0 | 2 | 1 | 1 | 1 | 5 | 0 |
| Clear cell adenocarcinoma ovary ($\eta$ + 6) | 0 | 0 | 1 | 5 | 0 | 2 | 1 | 1 | 2 | 6 | 0 |
| Endometrioid endometrial adenocarcinoma ($\eta$ = 10) | 0 | 0 | 2 | 8 | 0 | 0 | 6 | 2 | 2 | 10 | 0 |
| Papillary serous carcinoma endometrium ($\eta$ = 2) | 0 | 0 | 0 | 2 | 0 | 0 | 0 | 0 | 2 | 2 | 0 |
| Endocervical adenocarcinoma ($\eta$ = 7) | 2 | 0 | 2 | 3 | 2 | 2 | 1 | 0 | 2 | 5 | 0 |
| Colorectal adenocarcinoma ($\eta$ = 21) | 15 | 4 | 0 | 2 | 15 | 1 | 1 | 2 | 2 | 2 | 4 |
| Breast carcinoma ($\eta$ = 4) | 4 | 0 | 0 | 0 | 4 | 0 | 0 | 0 | 0 | 0 | 0 |
| Gastric adenocarcinoma ($\eta$ = 9) | 5 | 1 | 2 | 1 | 5 | 4 | 0 | 0 | 0 | 3 | 1 |
| Prostatic adenocarcinoma ($\eta$ = 4) | 4 | 0 | 0 | 0 | 4 | 0 | 0 | 0 | 0 | 0 | 0 |
| Pancreatic adenocarcinoma ($\eta$ = 6) | 2 | 0 | 0 | 4 | 2 | 3 | 1 | 0 | 0 | 4 | 0 |
| Gallbladder adenocarcinoma ($\eta$ = 2) | 2 | 0 | 0 | 0 | 2 | 0 | 0 | 0 | 0 | 0 | 0 |
| Lung adenocarcinoma ($\eta$ = 4) | 3 | 0 | 1 | 0 | 3 | 0 | 1 | 0 | 0 | 1 | 0 |

TABLE 1-continued

Specimens included in study together with immunohistochemical staining results

| Tumour | Staining intensity | | | | Percentage positivity | | | | | Membranous | Cytoplasmic |
|---|---|---|---|---|---|---|---|---|---|---|---|
| | Neg | Weak | Mod | Strong | 0 | + | ++ | +++ | ++++ | | |
| Mesothelioma (η = 10) | 6 | 0 | 2 | 2 | 6 | 1 | 1 | 1 | 1 | 2 | 2 |

EXAMPLE 4

Serological Test for the Detection of Sialylated SM047 Antigen

SM047-reactive molecules can be immunoprecipitated from the medium of cultured ovarian carcinoma cells and from the serum of patients with carcinoma of the ovary. Molecules bearing the SM047 epitope are also present in the serum of healthy subjects but these differ from the tumour associated ones in that they are electrophoretically heterogeneous whereas those shed by ovarian tumours are homogeneous and sialylated. The diagnostic test utilizes this difference and detects only the sialylated molecules.

Wells of an ELISA plate are coated with SM047 antibody to capture the tumour-associated as well as normal SM047 antigen from patients' sera. The immobilized tumour antigen but not the normal antigen is then detected by incubating with biotin-labelled lectin, which binds to the sialic acid residues on the tumour antigen, followed by streptavidin-labelled horseradish peroxidase which binds to the biotin. The optical density of the coloured product produced by the peroxidase substrate is read with an ELISA reader.

The following reagents are required:
Purified monoclonal antibody SM047.
Washing solution: phosphate-buffered saline (PBS) containing 0.05% Tween 20.
Blocking solution: 5% w/v skim milk powder in PBS.
Sera from patients and normal volunteers, diluted 1:4 or more in blocking solution.
Detecting reagent: Maackia amurensis lectin labelled with biotin.
Commercially available peroxidase-labelled streptavidin.
Commercially available tetramethylbenzidine (TMB) peroxidase substrate solution.
Stopping solution: 1M phosphoric acid.

The following is, by way of example, one method of purification. The SM047 hybridoma is grown in serum-free and protein-free medium (e.g. Sigma Hybrimax) and the spent medium collected. This can be concentrated by Amicon filtration to shorten the time required for loading the column. A column of Hydroxyapatite (Bio-Gel HTP, BIO-RAD #130-0420, or equivalent) is prepared by resuspending the fully hydrated material in 10 mM sodium phosphate pH 6.8 and a 5–10 ml column is prepared for processing about 500 ml conditioned medium. The column is washed with 10 column volumes of 10 mM sodium phosphate pH 6.8. The antibody solution is passed through the column and washed with 20 column volumes of 10 mM Na phosphate pH 6.8.

The antibody is eluted by raising the phosphate concentration in steps of 50 mM, 100 mM, 200 mM and 300 mM (or by applying a linear gradient of 120–300 mM Na phosphate pH 6.8). 1 ml fractions are collected and tested for protein. IgM comes off in a sharp peak and can be stored in the phosphate buffer or further concentrated by ammonium sulphate precipitation. The purity is checked by electrophoretic analysis (SDS-PAGE).

The column can be regenerated by washing in 1M NaCl in 10 mM Na phosphate pH6.8. The next step is to label the Maakia amurensis lectin (Sigma 18025 or equivalent) with biotin. Lectin is dissolved in 0.15M NaCl+0.1M NaHCO$_3$ at 2 mg/mL.

"Long-arm" biotin (Biotinamidocaproate-N-hydroxysuccinimide ester (Sigma B2643 or equivalent)) is dissolved at 2.5 mg/mL in dimethylsulphoxide (DMSO) and one-tenth volume of biotin solution is added to the lectin solution, and the reaction is allowed at room temp. for 2 hours. The product is dialysed against 0.2M NaCl+0.1M Tris pH7.4 and 0.1% sodium azide added.

The tests are conducted in duplicate in Nunc "Maxisorp" ELISA plates. All reagents are used at 100 μL per well except the blocking solution which is used at 250 μL per well. The plate is coated with purified SM047 antibody at 10 μg/mL in PBS and left overnight at 4 C. It is then washed three times. It is blocked for 1 hour at room temperature and the blocking solution then removed. The plate is incubated for 1 hour at room temperature with diluted patients' or control sera and then washed three times. It is then incubated for 1 hour at room temperature with biotin-labelled lectin, diluted 1:1000 in PBS and again washed three times. Finally it is incubated for ½ hour at room temperature with streptavidin-peroxidase diluted 1:1000 in PBS and then washed five times. The TMB substrate is added and after 10 minutes at room temperature the phosphoric acid solution is added.

The results are shown in Table 2. The optical density is read at 450 nm with an ELISA reader. In Table 2, the optical density readings for the detected sialyated SM047 antigen are expressed as a percentage of a mean optical density obtained for 5 normal control sera. The results for CA125 are given for comparison. As shown in Table 2, ovarian carcinoma has been proven in the patients A1 to A11.

TABLE 2

The serological test results

| | SMO47 | CA125 | DIAGNOSIS |
|---|---|---|---|
| A1 | 288% | 347.3 | recurrent ca ovary (died) |
| A2 | 280% | 1069.4 | recurrent serous cystadenoca of ovary |
| A3 | 271% | 350.3 | residual serous cystadenoca of ovary |
| A4 | 214% | | serous ca ovary (died) |
| A5 | 210% | 106.6 | recurrent serous cystadenoca of ovary |
| A6 | 180% | 382.1 | recurrent mixed epithelial cystadenoca of ovary |
| A7 | 162% | 59 | mucinous ca ovary, 10 days post-op |
| A8 | 135% | 202.3 | residual serous ca ovary, post-op |
| A9 | 103% | | ca uterus + ca ovary (endometrioid), 7d post-op |
| A10 | 90% | 257 | mucinous cystadenoca of ovary, "intestinal variant" |
| A11 | 56% | 36.2 | undifferentiated ca ovary |

Immunoprecipitation Results:

In immunoprecipitation and immunoblots of lysates of cultured ovarian carcinoma cells SM047 bound molecules with an $M_r$>200 kDa (FIG. 1, lane 1). SM047 immunoprecipitates antigenic molecules with heterogeneous electrophoretic mobilities from the sera of normal subjects and from patients with ovarian carcinoma. Immunoprecipitates of SM047-reactive molecules from ovarian carcinoma cell lysate and from normal and patients' sera were analysed by SDS-PAGE in 4.5–15% gradient gels, of which FIG. 1 is an example. After electrophoresis the precipitates were transferred electrophoretically to a PVDF membrane and reacted with SM047 (FIG. 1, lanes 1–3) or J138 control antibody (lanes 4–6) followed by a peroxidase detection system with chemiluminescent substrate. The cell lysate (lane 1) showed a distinct band which just entered the separating gel, whereas in the normal serum (lane 3) antigers expressing the SM047 epitope were heterogeneous and of lower $M_r$, giving the appearance of a 'smear' in the Western blot. The serum from the patient (lane 2) contained both the high $M_r$ and the lower $M_r$ heterogeneous species, the latter being slightly reduced in quantity in the serum of the patient.

With this technique similar high $M_r$ bands could be identified in seven of 15 sera from patients with ovarian malignancy. A homogeneous, high $M_r$ band similar to that precipitated from the UWOV1 cell lysate was also immunoprecipitated from the conditioned medium of these ovarian carcinoma cells (not shown), which confirms that the antigen is shed from the cells into the surrounding medium. The tumour-associated antigen present in the serum of patients with carcinoma of the ovary could thus be explained by shedding from the tumour into the circulation.

Figure 2:
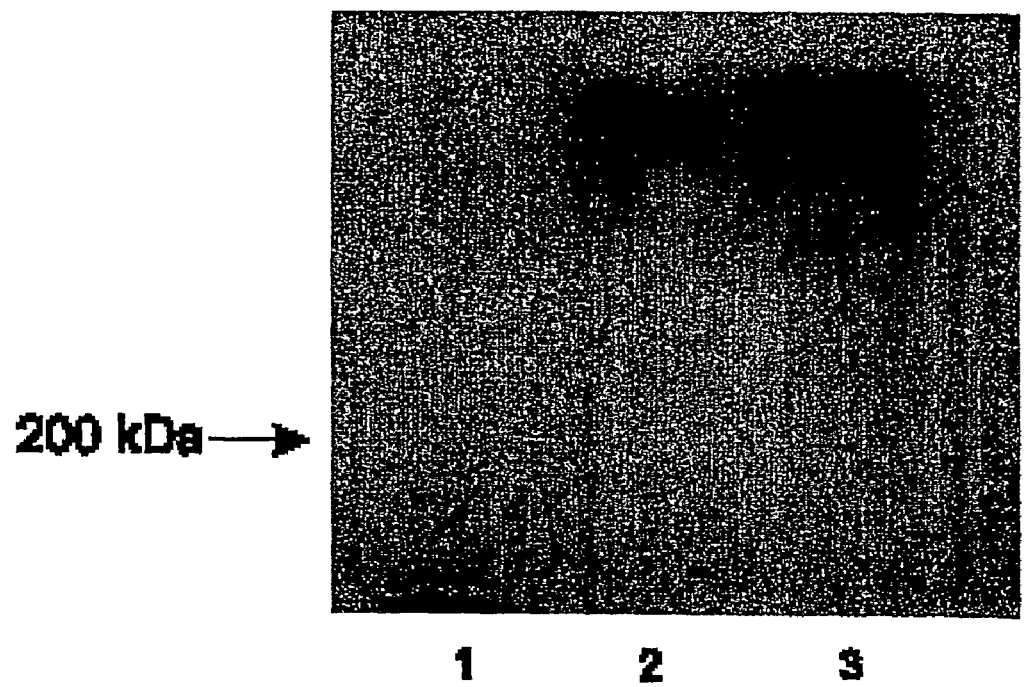
FIG. 2 shows SM047 immunoprecipitates probed for sialic acid residues. SM047 immunoprecipitates from UWOV1 lysate, patient's serum and pooled normal serum were prepared and SDS-PAGE and electroblotting performed. The proteins on the membrane were oxidized with metapriodate at 4° C. and labelled with biotin hydrazide according to instructions with the glycoprotein detection kit. The membrane was finally treated with streptavidin-peroxidase and chemiluminescent substrate as for immunoblots. Lane 1, pooled normal serum; lane 2, patient's serum; lane 3 UWOV1 lysate.

The ovarian carcinoma-associated high molecular weight form of the SM047 antigen is sialylated; the SM047 antigens in normal sera are not. SM047 immunoprecipitates of pooled normal serum, of serum from a patient with ovarian cancer and UWOV1 cell lysate were electrophoresed in a 7% acrylamide gel and transferred electrophoretically to PVDF membrane. The transferred antigens were then oxidized with metaperiodate at 4° C. and labelled with biotin hydrazide to detect sialylated glycoprotein.[10] The biotin label was detected with streptavidin-peroxidase as in the immunoblots. The result (FIG. 2) shows dearly that the immunoprecipitated antigens from pooled normal serum were not sialylated (lane 1), whereas those from a patient's serum (lane 2) and carcinoma cell lysate (lane 3) were.

The SM047 antigen has characteristics of a cell-associated proteoglycan. To analyse immunoprecipitates of metabolically labelled SM047 antigen, UWOV1 were incubated, either for 2 h or overnight, with $^{35}$S-methionine, $^{3}$H-leucine or $^{35}$S-sulphate, in medium deficient of these precursors, using standard experimental protocols.[11] No detectable labelled antigen could be precipitated from the cell lysates labelled with $^{35}$S-methionine or $^{3}$H-leucine. On the other hand, lysates of UWOV1 cells that had been incubated overnight with $^{35}$S-sulphate revealed a homogeneous band of radioactive antigen similar to the sialylated tumour antigen when immunoprecipitated with SM047 and analysed by SDS-PAGE and fluorography (not shown).

The SM047 tumour antigen therefore has characteristics of a cell-associated proteoglycan but it is not known if the normal heterogeneous form of the antigen is sulphated.

The above results show that there was strong positive membranous staining of most non-mucinous ovarian adenocarcinomas but no staining of the majority of mucinous tumours with SM047. Moreover, mucinous tumours, when positive, usually exhibited weak cytoplasmic staining. This immunohistochemical profile is similar to that of CA125 which is widely used In pathological practice when attempting to confirm an ovarian primary for an adenocarcinoma.

Such results suggest that SM047 staining is of value in the distinction between a primary, ovarian endometrioid adenocarcinoma, which usually exhibits strong membranous positivity, and a colonic adenocarcinoma which is usually either negative or exhibits weak cytoplasmic immunoreactivity.

Adenocarcinomas of the stomach, pancreas and biliary tree when metastatic to the ovary may also closely resemble a primary ovarian adenocarcinoma,[12] especially of mucinous type. With these adenocarcinomas, the CK profile is similar to that of a primary ovarian adenocarcinoma. Most pancreatic adenocarcinomas studied exhibited strong membranous staining with SM047 and the antibody is of value in distinguishing a primary ovarian mucinous tumour (usually SM047−) from a metastatic pancreatic adenocarcinoma (usually SM047+).

Diffuse involvement of the peritoneal cavity by ovarian serous adenocarcinoma or primary peritoneal serous adenocarcinoma may closely mimic mesothelioma clinically and histologically. Immunohistochemistry may facilitate the distinction but there is considerable overlap. SM047 is of some value, when used as part of a panel, since strong membranous positivity is found in most serous adenocarcinomas whereas most mesotheliomas are negative or exhibit cytoplasmic staining. However, occasional mesotheliomas exhibit strong membranous Immunoreactivity and there is strong membranous staining of normal mesothelial cells.

CA125 is widely used as a serum marker of ovarian adenocarcinoma.[13] However, a raised serum CA125 is not specific for ovarian adenocarcinoma, this being found in a variety of conditions, especially when there is widespread peritoneal disease. This can be attributed to the production of CA125 by mesothelial cells.[14] The SM047 antigen according to the invention was detected in sera of patients with ovarian malignancy but also in normal human serum. However, there was a consistent biochemical difference between normal and tumour-associated SM047-reactive antigens, the former being non-sialylated and the latter sialylated.

In the present invention, it shows that most non-mucinous ovarian adenocarcinomas as well as adenocarcinomas primary elsewhere in the female genital tract are SM047+. Accordingly, the monoclonal antibody SM047 is useful when used as part of a larger panel, in determining the site of origin of an adenocarcinoma.

REFERENCES

1. McCluggage W G. Recent advances in immunohistochemistry in the diagnosis of ovarian neoplasms (review article). *J. Clin. Pathol.* 2000; 53; 327–334.
2. Cheung A N Y, Chin P M, Khoo U S. Is immunostaning with HAM 56 antibody useful in identifying ovarian origin of metastatic adenocarcinomas *Hum. Pathol.* 1997; 28; 91–94.
3. Loy T S, Quesenberry J T, Sharp S C, Distribution of CA125 in adenocarcinomas: an immunohistochemical study of 481 cases. *Am. J. Clin. Pathol.* 1992; 98; 175–179.
4. Wauters C C A P, Smedts F. Gerrits L G M, Bosman F T, Ramaekers F C S, Keratins 7 and 20 as diagnostic markers of carcinomas metastatic to the ovary. *Hum. Pathol.* 1995; 26; 882–885.

5. Berezowski K. Stasny J F, Kornstein M J. Cytokeratins 7 and 20 and carcinoembryonic antigen in ovarian and colonic carcinoma. *Mod. Pathol.* 1996; 9: 426–429.
6. Golombick T, Dansey R D, Bezwoda W R et al. Establishment and charcterisation of two new human ovarian cancer cell lines, UWOV1 and UWOV2, and a subline UWOV2 (sf), growing in serum-free culture; growth characteristics, bio-chemical and cytogenetic studies. *In Vitro Cell Dev. Biol.* 1990; 26; 447–454.
7. Warren L, Glick M C, Nass M K. Membranes of animal cells, 1. Methods of isolation of the surface membrane, *J. Cell Physiol.* 1966; 68; 269–288.
8. Veenstra H, Dowdle E B. Multi-well cell monolayers for immunocytochemistry. *J. Immunol. Methods* 1992; 146; 257–258.
9. Jones P P. Analysis of radiolabelled lymphocyte proteins by one- and two-dimensional polyacrylamide gel electrophoresis. In: Mishell B B Shiigi S M, eds. *Selected methods in cellular immunology*. San Francisco: W H Freeman, 1980; 398–440.
10. Bayer E A, Ben-Hur H, Wilchek M. Analysis of proteins and glycoproteins on blots. *Methods Enzymol.* 1990; 184; 415–427.
11. Bonifacino S. Biosynthetic labelling of proteins. In: Coligan J E, Kruisbeek A M, Margulies D H, Shevach E M, Strober W. eds. *Current protocols in immunology*. New York; John Wiley & Cons, Inc., 1991; 8.12.1–8.12.9.
12. Young R H, Hart W R. Metastases from carcinomas of the pancreas simulating primary mucinous tumors of the ovary. A report of seven cases. *Am. J. Surg. Pathol.* 1989; 13; 748–756.
13. Jacobs I, Bast R C. The CA125 tumour associated antigen; a view of the literature. *Hum Reprod.* 1989; 4; 1.
14. Nouwen E J, Pullet D E, Edekens M W et al. Immunohistochemical localisation of placental alkaline phosphatase, carcinoembryonic antigen, and cancer antigen 125 in normal and neoplastic human lung. *Cancer Res.* 1986; 46; 866–876.

The invention claimed is:

1. A monoclonal antibody designated SM047, which is produced by hybridoma cells deposited with the ECACC, bearing Accession number 01082905, and which is reactive against ovarian carcinoma.

2. A hybridoma cell producing a monoclonal antibody designated SM047, said hybridoma cell deposited with the ECACC, bearing Access number 01082905, and said antibody reactive against ovarian carcinoma.

3. A process for producing a monoclonal antibody comprising culturing hybridoma cells deposited with the ECACC bearing Accession number 01082905 which produce a monoclonal antibody designated SM047 and purifying the monoclonal antibody from the culture thus obtained.

4. A diagnostic aid comprising: a) a monoclonal antibody designated SM047, which is produced by hybridoma cells deposited with the ECACC bearing the Accession number 01082905 and b) a detectable label, whereby the binding of the antibody in step (a) can be detected.

5. A diagnostic aid as claimed in claim 4, wherein the label is selected from the group consisting of enzymes, radiolabels, chromophores and fluorescers.

6. A diagnostic aid as claimed in claim 4 for use in the detection of carcinoma.

7. A diagnostic aid as claimed in claim 6, wherein the carcinoma is an ovarian carcinoma or female genital tract carcinoma.

8. A method for detecting carcinoma which comprises contacting a monoclonal antibody designated SM047, which is produced by the hybridoma cells deposited with the ECACC, bearing Accession number 01082905, and which is reactive against ovarian carcinoma with a human tissue or serum sample, and detecting the interaction of said antibody with any antigenically-corresponding carcinoma cells or antigenic determinants in said sample.

9. A method as claimed in claim 8, wherein the carcinoma is an ovarian carcinoma or female genital tract carcinoma.

10. The method as claimed in claim 8, wherein the interaction is detected by immunohistological staining.

11. A monoclonal antibody as claimed in claim 1 for use in the manufacture of a diagnostic aid for detecting carcinoma.

12. A monoclonal antibody designated SM047, which is produced by hybridoma cells deposited with the ECACC, bearing Accession number 01082905, and which is reactive against ovarian carcinoma supplied with instructions for the use thereof in detecting carcinomas.

13. The monoclonal antibody as claimed in claim 12 wherein the instructions are in printed or written form.

14. The monoclonal antibody as claimed in claim 13 supplied in a package or container having said instructions provided therein or thereon.

* * * * *